United States Patent [19]

Volante et al.

[11] Patent Number: 4,814,452

[45] Date of Patent: Mar. 21, 1989

[54] ENANTIOSELECTIVE SYNTHESIS OF 1,3,4,6,7,12B(S)-HEXAHYDRO-2H-BENZO[b-]FURO[2,3-a]QUINOLIZIN-2-ONE

[75] Inventors: Ralph P. Volante, East Windsor; Edward Corley, Old Bridge; Ichiro Shinkai, Westfield, all of N.J.

[73] Assignee: Merck & Co., Inc., Rahway, N.J.

[21] Appl. No.: 881,993

[22] Filed: Jul. 3, 1986

[51] Int. Cl.[4] ......................................... C07D 491/048
[52] U.S. Cl. ........................................ 546/89; 546/8; 546/13; 546/71; 549/467
[58] Field of Search ................ 546/8, 13, 89; 549/467

[56] References Cited

U.S. PATENT DOCUMENTS 4,617,305 10/1986 Hannart .................................. 546/18
4,710,504 12/1987 Baldwin et al. ....................... 546/18

FOREIGN PATENT DOCUMENTS 154142 9/1985 European Pat. Off. .

OTHER PUBLICATIONS

Tet. Letters, 5031, (1984), Braun & DeVant.

*Primary Examiner*—Donald G. Daus
*Assistant Examiner*—Andrew Rozycki
*Attorney, Agent, or Firm*—William H. Nicholson; Michael C. Sudol, Jr.

[57] ABSTRACT

An enantioselective synthesis of 1,3,4,6,7,12b(S)-hexahydro-2H-benzo[b]furo[2,3-a]quinolizin-2-one provides a key intermediate for the preparation of the $\alpha_2$-adrenergic antagonist (2R,12bS)-N-(1,3,4,6,7,12-hexahydro-2H-benzo[b]furo[2,3-a]quinolizin-2-yl)-N-methyl-2-hydroxyethanesulfonamide hydrochloride, useful as an anti-depressant.

4 Claims, No Drawings

ENANTIOSELECTIVE SYNTHESIS OF 1,3,4,6,7,12B(S)-HEXAHYDRO-2H-BENZO[b]FURO[2,3-a]QUINOLIZIN-2-ONE

BACKGROUND OF THE INVENTION

Published European Patent Application No. 154,142, and U.S. application Ser. No. 755,863, now abandoned, filed July 17, 1985 which are incorporated herein by reference, which was refiled as Ser. No. 885,511, now U.S. Pat. No. 4,690,928 disclose the compound (2R,12bS)-N-(1,3,4,6,7,12-hexahydro-2H-benzo[b]furo[2,3-a]quinolizin-2-yl)-N-methyl-2-hydroxyethanesulfonamide and the enantiomeric quinolizin-2-one intermediate and alternate routes for their syntheses. With the present invention there is provided a new enantioselective route for the synthesis of the intermediate.

The quinolizin-2-one intermediate was previously prepared by standard chemical resolution of racemic ketoamine with L-(+)di-p-toluoyl tartaric acid to give (−)12b(S)-ketoamine in 30–35% yield. A resolution process has a maximum yield of 50%, thus one must always lose 50–65% of the total racemic material being resolved. The present invention produces 12b(S)-ketoamine of greater than 90% optical purity, with optimization to 99% optical purity possible. This invention obviates the need for chemical resolution and, thus, provides a more efficient synthesis of the (−)-12b(S)-ketoamine.

DETAILED DESCRIPTION OF THE INVENTION

The novel process of this invention is an enantioselective synthesis of 1,3,4,6,7,12b(S)-hexahydro-2H-benzo[b]furo[2,3-a]quinolizin-2-one comprising the steps:

(1) treating a compound of structural formula:

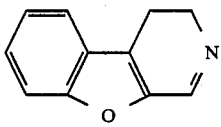

in the presence of a Lewis acid with a non-racemic acetate enolate derivative of the formula:

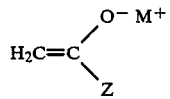

wherein the Lewis acid is selected from $BF_3 \cdot O(R)_2$, $TiX_4$, $Ti(OR)_2X_2$, $Ti(OR)_3X$, $Ti(OR)X_3$, $ZnX_2$, $MgX_2$, $SnX_4$, and $SnX_2$, wherein R is $C_{1-5}$alkyl, and X is halogen, such as chloro, bromo, fluoro, or iodo; and Z is

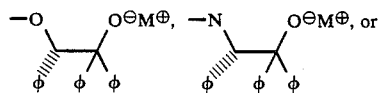

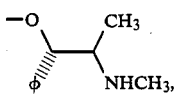

and $M^+$ is $Na^+$, $Li^+$, $K^+$, $Mg^{++}$, $Zn^{++}$, B, $Sn^{++}$, $Sn^{+4}$, $Ti^{+4}$ or the like.

It is preferred that the Lewis acid is $Ti(OR)_2X_2$, wherein R is 2-propyl and X is chloro; that Z is

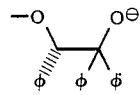

and that $M^+$ is $Li^+$.

The activated imine is formed in an inert organic solvent such as a chlorinated hydrocarbon such as methylene chloride, chloroform, 1,2-dichloroethane, or the like at about 20° to 30° C. over a period of about 0.25 to one hour followed by addition to a solution of the acetate enolate in an ethereal solvent such as THF, diethyl ether, 1,2-dimethoxyethane or the like at about −70° to −100° C., dry-ice/acetone temperature being convenient and maintaining that temperature about 10 to 30 minutes and then quenching with aqueous ammonium chloride to produce a compound of structure:

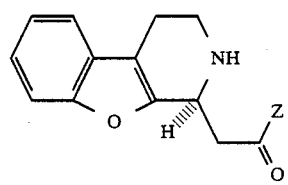

(2) treating the product of Step 1 with an excess of a $C_{1-3}$alkyl acrylate such as ethyl acrylate at about 45° to 100° C. for about 1 to 4 hours to produce a compound of structure:

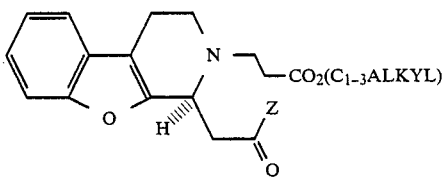

(3) treating the product of Step 2 with a strong base such as sodium hydride in an inert organic solvent such as benzene, toluene or the like and a trace of a lower alkanol at about 20° to 50° C. followed by heating to about 80° to 120° C. for 12 to 24 hours, followed by cooling to about 20° to 50° C., adding water and a lower alkanol and heating to about 80° to 100° C. for about 12 to 24 hours, to produce the compound of structural formula:

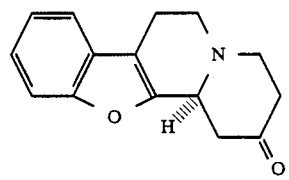

This key chiral quinolizin-2-one is readily converted to the known $\alpha_2$-antagonist (2R,12bs)-N-(1,3,4,6,7,12-hexahydro-2H-benzo[b]furo[2,3-a]-quinolizin-2-yl)-N-methyl-2-hydroxyethanesulfonamide as described in the following Example, Steps H and I and in European Patent Application No. 154,142 and U.S. application Ser. No. 755,863, filed July 17, 1985, the disclosure of which are incorporated herein by reference.

EXAMPLE
(2R,12bs)-N-(1,3,4,6,7,12-Hexahydro-2H-benzo[b]furo[2,3-a]quinolizin-2-yl)-N-methyl-2-hydroxyethanesulfonamide Step A: Preparation of 3-Cyanomethylbenzo[b]furan

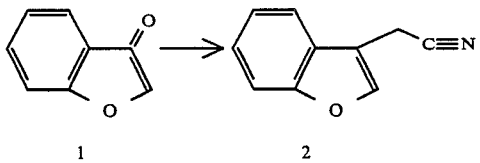

NaH (54 g of a 50% oil suspension; 1.12 mol) was placed in a 3 L 3-neck RB flask equipped with a mechanical stirrer and washed twice with hexane. Dry THF (400 ml) was added followed by the dropwise addition of a solution of diethylcyanomethyl phosphonate (199.2 g; 1.12 mol) in 400 ml of THF. After the addition was complete, the reaction was stirred an additional 30 minutes until gas evolution ceased. A solution of 1 (150.1 g; 1.12 mol) in 1 L of THF was added dropwise at room temperature. The reaction was refluxed for 1.5 hours. After cooling, the solvent was removed in vacuo. The residue was dissolved in ether and acidified with concentrated HCl. The ether layer was washed with 6N HCl (3×300 ml), H$_2$O, brine, dried (Na$_2$SO$_4$), filtered, and concentrated. The crude product was distilled to afford 116 g (66%) of 2 b.p. (0.7 Torr) 110°-120° C.

Step B: Preparation of 3-(2-aminoethyl)benzo[b]furan

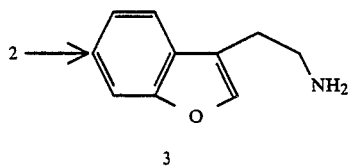

A solution of 3.1 g of nitrile 2 was treated with 2.4 g of Raney Nickel in 40 ml methanol at 40 PSI of hydrogen for 12 hours or until a theoretical amount of hydrogen was absorbed (2.0 equivalents). The catalyst was removed by filtration and the methanol was removed in vacuo to give 2.2 g (71%) yield of amine 3.

Step C: Preparation of 3-(formamidoethyl)benzo[b]furan

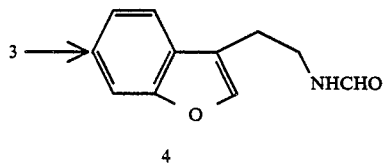

The crude 3 (121 g) was heated in 300 ml of ethylformate for 3 hours at 60° C. Excess ethylformate was evaporated, and the residue dissolved in CH$_2$Cl$_2$. The organic phase was washed with 2N HCl, brine, dried (Na$_2$SO$_4$), charcoaled, and concentrated to 118 g of crude product which was used without further purification.

Step D: Preparation of 3,4-Dihydrobenzo[b]furo[2,3-c]pyridine

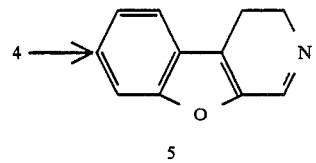

Amide 4 (94 g) was added to a mixture of 70.5 g of P$_2$O$_5$ dissolved in 477 ml of methane sulfonic acid at 90° C. The solution was then stirred for 2 hours at 85°-90° C. After cooling the reaction mixture was poured into 500 ml of water keeping the temperature <50° C. The aqueous solution was then made basic by the addition of aqueous ammonium hydroxide solution causing imine 5 to precipitate. The precipitate was collected by filtration and dried to give 47.5 g (92%) of a tan colored solid.

Step E: Preparation of 12b(S)-1',1',2'-Triphenylethanol-2'-acetoxy-2-yl-1,2,3,4-tetrahydrobenzofuro[2,3-c]pyridine

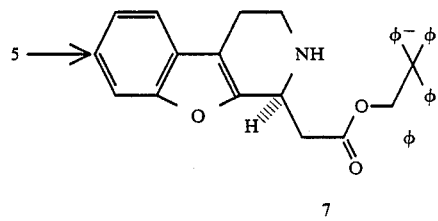

To a solution of 3.3 mL titanium tetraisopropoxide and 1.25 mL of titanium tetrachloride in 45 mL of methylene chloride at 22°-24° C. was added 3.4 g of 3,4-dihydrobenzo[b]furo[2,3-c]pyridine. This solution was stirred at 22°-24° C. for 30 minutes and was then added dropwise over 50 minutes to a solution of dilithio(S)-(−)-triphenyldiol acetate (21 mmol) in 50 mL of tetrahydrofuran at −70° to −78° C. (Dilithio(S)-(−)-triphenyldiol acetate was prepared in the standard manner by deprotonation of the corresponding acetate ester with 2.0 equivalents of lithium diisopropylamide in tetrahydrofuran at −20° to 0° C., (M. Braun and R. Devant, Tet. Lett. 5031, 1984)). The mixture was stirred at −78° C. for 15 minutes and quenched at −78° C. by the addition of 100 mL of saturated ammonium chloride solution and warming to 22°-24° C. The mixture was then extracted with methylene chloride and the organic phase dried over sodium sulfate and concentrated in vacuo to give 10.5 g of 12b(S)-amino-ester as a solid. Proton NMR analysis showed the amino-ester to be a 90:10 ratio of the desired 12bS to 12bR diastereomers.

Step F: Preparation of (S)-1',1',2'-Triphenylethanol-2'-acetoxy-2-yl-N-[ethylpropionate-3-yl]-1,2,3,4-tetrahydrobenzofuro[2,3-c]pyridine

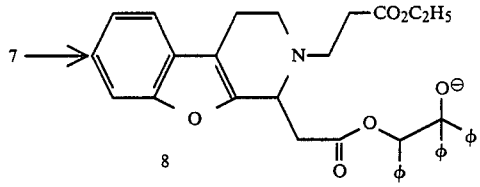

The amino-ester (10.5 g) of Step E was heated at 60°–75° C. for 2 hours in excess ethyl acrylate (25 ml) to give a quantitative yield (12.5 g) of diester after concentration in vacuo to remove excess ethyl acrylate.

Step G: Preparation of 1,3,4,6,7,12b(S)-hexahydro-2H-benzo[b]furo[2,3-a]quinolizine-2-one

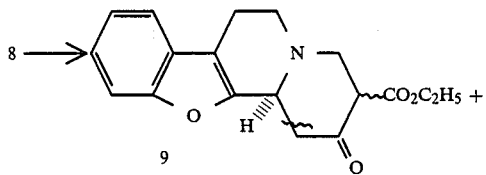

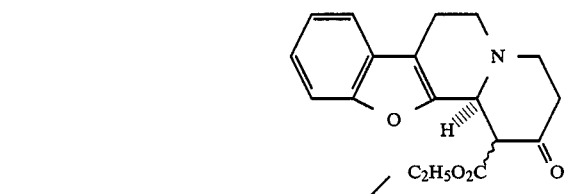

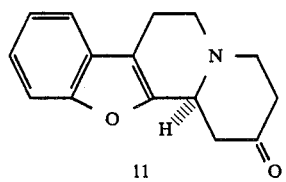

Diester 8 (900 mg) was dissolved in 10 ml of toluene and added to a suspension of 96 mg of 60% sodium hydride at 22°–24° C. Ethanol (10 microliters) was added and the mixture was heated at reflux under nitrogen for 16 hours. The reaction mixture was cooled to 22° C. and quenched by the addition of 10 ml H$_2$O. Methanol (3.5 ml) was added and the solution was again heated at reflux for 16 hours. The reaction mixture was cooled to 22° C. and acidified with 3N HCl to pH 2.0. The mixture was then diluted with 25 ml of water and extracted with methylene chloride. The organic layer was dried over sodium sulfate and concentrated in vacuo to give 185 mg of keto-amine 11 as a white solid (55% yield) [α]$_D^{25}$ = −82° vs. [α]$_D^{25}$ (lit) = −84°.

Step H: Preparation of (2R,12bS)-1,3,4,6,7,12b-hexahydro-2-methylamino-2H-benzo[b]furo[2,3-a]quinolizine

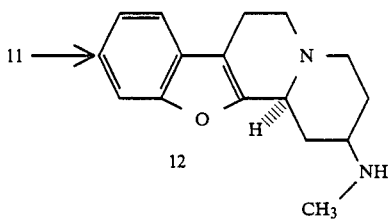

The ketone 11 (25.5 g; 0.106 mol) was added to a mixture of ether (360 ml) and benzene (210 ml) under N$_2$ in a flame-dried 1 L 4-neck RB flask equipped with mechanical stirrer, condenser, addition funnel, and thermometer. The reaction was cooled to −10° C. in an ice-acetone bath. Methylamine (22.8 g; 26.7 ml; 0.74 mol) was added, followed by dropwise addition of TiCl$_4$ (10.2 g; 5.93 ml; 0.054 mol) in 25 ml benzene. The reaction was stirred at −10° to 0° C. for 30 minutes, and then at room temperature for 2 hours. The precipitate was removed by filtration and washed with benzene/ether (2:1). The filtrate was concentrated to dryness, and the residue dissolved in 700 ml of absolute ethanol. Sodium borohydride (4.74 g; 0.125 mol) was added, and the reaction stirred overnight at room temperature. The reaction was quenched by addition of 500 ml H$_2$O, and the ether removed in vacuo. The precipitate was filtered, washed with H$_2$O, and dried to yield 28.8 g of the crude product. This material was recrystallized from 300 ml of ethanol/H$_2$O (1:1) to afford 21.3 g of colorless crystals which analyzed as the 2.5 hydrate. The crystals were dissolved in CH$_2$Cl$_2$ and dried (Na$_2$SO$_4$). Evaporation of the solvent yielded 20.5 g of the product: m.p. 77°–79° C.; [α]$_D$ = −71° (C=1 in CHCl$_3$).

Step I: Preparation of (2R,12bS)-N-1,3,4,6,7,12b-hexahydro-2H-benzo[b]furo[2,3-a]quinolizin-2-yl)-N-methyl-2-hydroxyethanesulfonamide

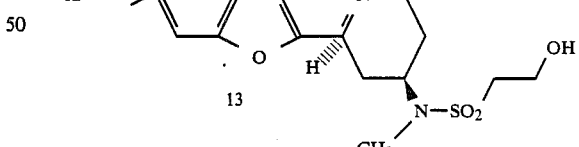

Solutions of 2-hydroxyethanesulfonyl chloride (20.2 g; 0.14 mol) in 100 ml of CH$_3$CN and (C$_2$H$_3$)$_3$)N (14.3 g; 19.7 ml; 0.14 mol) in 100 ml of CH$_2$Cl$_2$ were added simultaneously by means of a dual syringe drive to a solution of 12 (17.9 g; 0.07 mol) in 1600 ml of a 1:1 mixture of CH$_3$CN and CH$_2$Cl$_2$. After 15 minutes the solvent was evaporated and the residue partitioned between CH$_2$Cl$_2$ and H$_2$O. The organic phase was separated and washed with H$_2$O, brine, and dried (Na$_2$SO$_4$). The solvent was evaporated and the residue chromatographed over silica gel, eluting with CHCl$_3$ saturated with NH$_3$. The product obtained (14(—GO—TO—

GL—) converted to the hydrochloride salt by adding C₂H₅OH—HCl to a solution of the base in ethylacetate. There was obtained 14 g of the product: m.p. 270°-272° C.; [α]$_D$=13° (C=1 in CH₃OH).

What is claimed is:

1. A compound of structural formula:

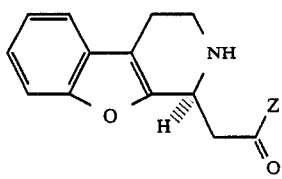

wherein Z is

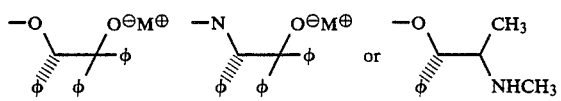

and M⁺ is Na⁺, Li⁺, K⁺, Mg⁺⁺, Zn⁺⁺, B, Sn⁺⁺, Sn⁺⁴ or Ti⁺⁴.

2. The compound of claim 1 wherein M⁺ is Li⁺ and Z is

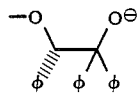

3. A compound of the structural formula:

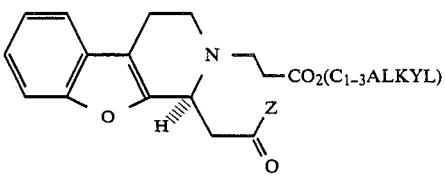

wherein Z is

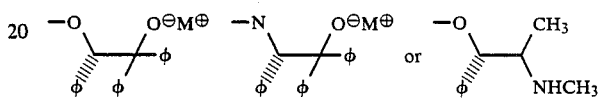

and M⁺ is Na⁺, Li⁺, K⁺, Mg⁺⁺, Zn⁺⁺, B, Sn⁺⁺, Sn⁺⁴ or Ti⁺⁴.

4. The compound of claim 3 wherein M⁺ is Li⁺ and Z is

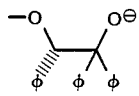

* * * * *